United States Patent [19]

Marx et al.

[11] Patent Number: 4,842,608
[45] Date of Patent: Jun. 27, 1989

[54] FLUCTUATING VOLUME ADJUSTABLE PREPARATORY BELOW KNEE PROSTHETIC SOCKET

[75] Inventors: Herbert W. Marx; Norbert Marx, both of West Islip, N.Y.

[73] Assignee: Ortho-Bionics Laboratory, Inc., South Ozone Park, N.Y.

[21] Appl. No.: 148,933

[22] Filed: Jan. 27, 1988

[51] Int. Cl.⁴ ............................................. A61F 2/78
[52] U.S. Cl. ...................................................... 623/33
[58] Field of Search ................................... 623/33, 37

[56] References Cited

U.S. PATENT DOCUMENTS

| | | | |
|---|---|---|---|
| 2,229,728 | 1/1941 | Eddells | 623/36 |
| 2,808,593 | 10/1957 | Andersen | 623/33 |
| 3,545,009 | 12/1970 | Colley | 623/33 |
| 3,889,301 | 6/1975 | Bonner | 623/37 |
| 4,655,779 | 4/1987 | Janowiak | 623/37 |

FOREIGN PATENT DOCUMENTS

| | | | |
|---|---|---|---|
| 2032281 | 5/1980 | United Kingdom | 623/33 |
| 2103490 | 2/1983 | United Kingdom | 623/33 |

Primary Examiner—Richard J. Apley
Assistant Examiner—James Prizant
Attorney, Agent, or Firm—Schweitzer & Cornman

[57] ABSTRACT

A fluctuating volume adjustable prosthetic socket for below-the-knee amputees comprising a generally hollow main body support of rigid plastic; a posterior popliteal section of rigid plastic generally contoured to conform to the posterior anatomy of the knees; elasticized sleeve means supported at lower portions of said posterior popliteal section; and cooperating locking means disposed on said posterior section and said main support section for adjustably joining said sections for controlled limited anterior-posterior displacement with respect to each other.

8 Claims, 5 Drawing Sheets

FIG. 4
FIG. 5
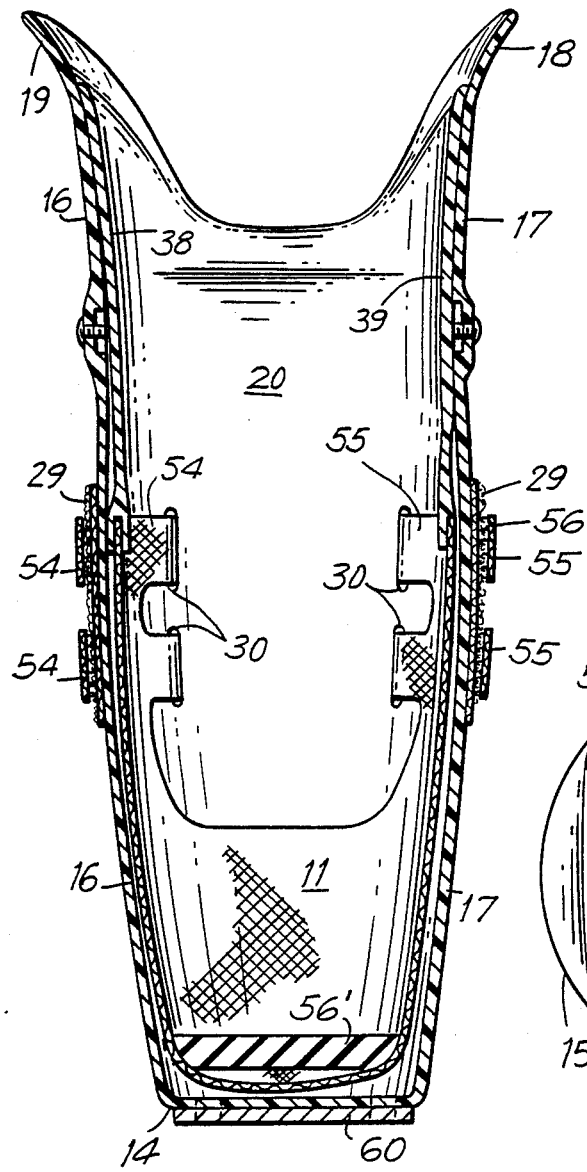
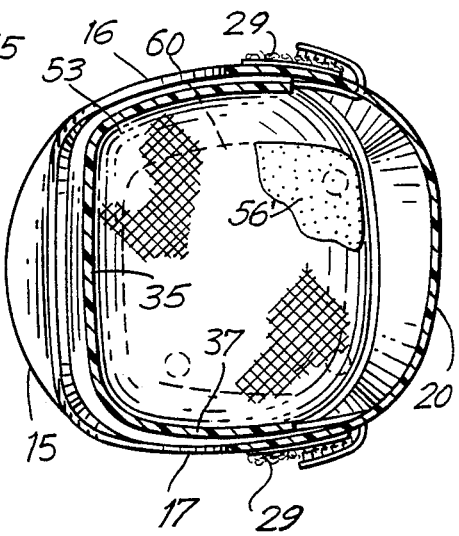

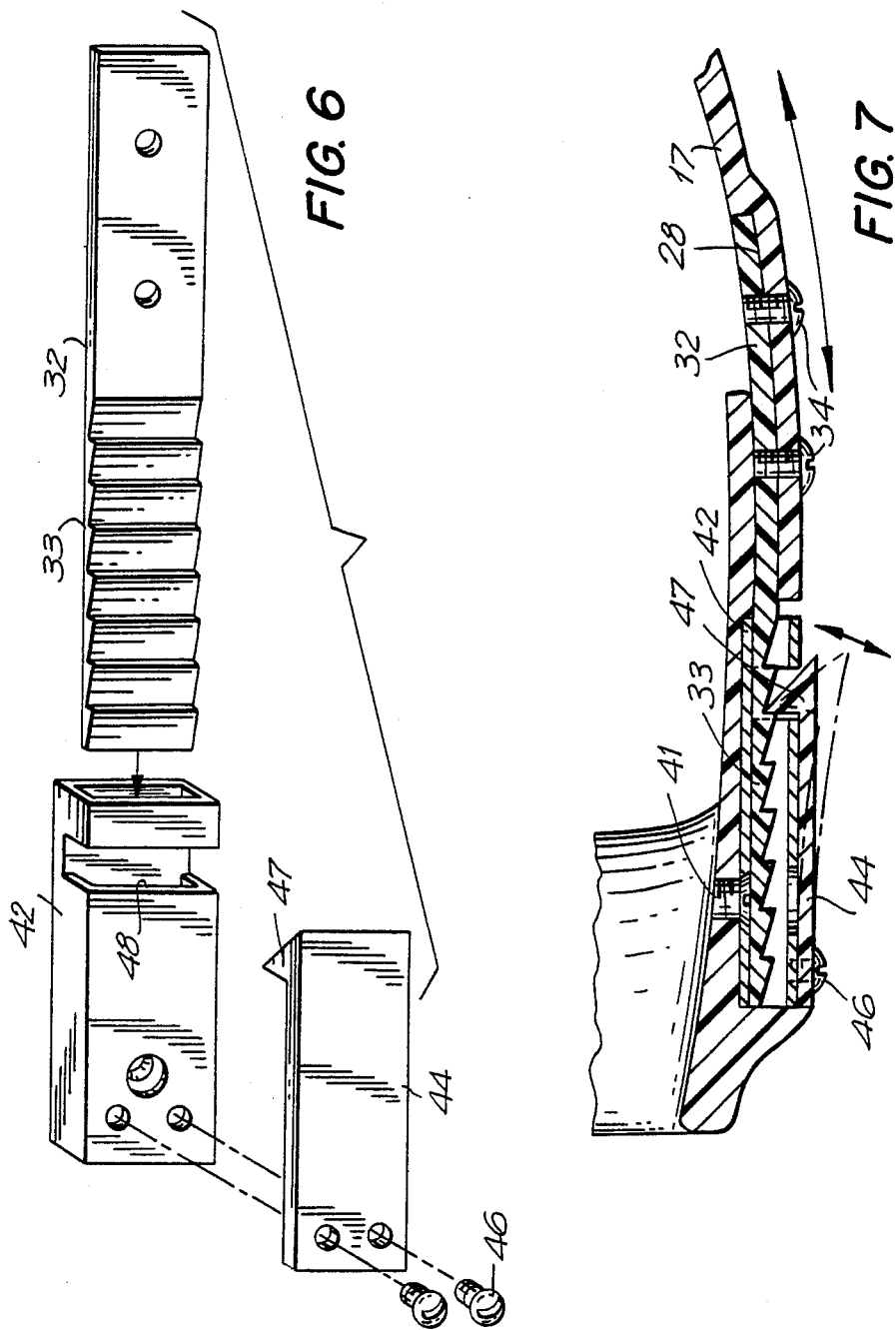

FLUCTUATING VOLUME ADJUSTABLE PREPARATORY BELOW KNEE PROSTHETIC SOCKET

BACKGROUND OF INVENTION

This invention is directed to a multi-directional adjustable prosthetic socket for a post operative amputee having a newly residual limb. Persons who have lost their limb due to amputation are usually custom fitted, shortly after surgery, with a preparatory or temporary prosthetic device for use prior to fitting with a permanent prosthetic limb. These devices must be custom made because of the individual physiological difference in the residual limb volume, including but not limited to the length of the residual limb. In addition, these preparatory (for eventual replacement by permanent sockets), below the knee, prosthetic sockets must be interchanged frequently because of the gradual reduction of the initial post-operative edema and the reduction in stump volume due to compression within the prosthetic socket. Heretofore, prosthetic sockets of this type could not be mass produced resulting in a major cost to below-knee amputees for custom-made prostheses.

For these patients, volume changes in their below-the-knee residual limbs occur mainly in reductions in the posterior distal aspects as viewed in the saggital plane, reductions in the medial lateral and distal aspect as viewed in the frontal plane, and reduction in the popliteum area. These volume changes, heretofore, have been accommodated only by custom redesigning and custom making the prosthetic socket for the changing stump.

SUMMARY OF THE INVENTION

With the specific areas of stump volume reduction in mind, an adjustable below-knee prosthetic socket has been developed for mass production in a series of four sizes, each of right limb and left limb design, to accommodate virtually all lower limb, mid-calf amputees. The anterior section and main support of the prosthetic socket is designed to accommodate the diameter of the knee as viewed in the frontal plane and is made of rigid plastic. In accordance with the invention, it provides support in the patella tendon area and, importantly, has a new special ratchet-like mechanism or a screw jack mechanism incorporated therein to accommodate precise adjustments in the anterior-posterior dimension. Accordingly, the temporary or preparatory socket will receive residual limbs of various sizes in that dimension and also will allow for changes when reduction of stump volume occurs in the popliteum area.

The lower section of this anterior part of the new and improved socket is slotted in the medial and lateral aspect to facilitate strap adjustments of an adjustable distal elasticized sleeve. The lowermost portion of this main support is provided with a metal plate to allow universal attachment of most endoskeletal shank and foot prosthetic components. In its posterior aspect, the new socket is provided with a calf-engaging member of rigid plastic construction. Thus, the new socket of rigid plastic provides resistance when the person wearing this socket forcefully flexes the knee. In addition, the anterior section and main support are designed to embrace the medial and lateral condyles of the femur providing medial and lateral stability to the knee joint and providing partial suspension on the residual limb.

In accordance with the principles of the invention, the posterior popliteal section is equipped on the medial and lateral aspect with the female part of the ratchet mechanism. This is in the form of a rectangular channel having a tongue on each of its long sides for purpose of attachment to the posterior section. The rectangular channel, in its anterior part, is provided with a slot in the top surface to accommodate a nylon spring with a ratchet tooth on its under surface engaging with corresponding hooks on the male member of the new ratchet mechanism. The posterior popliteum section, which is specially contoured to accommodate and to conform to the anatomy of the posterior aspect of the patient's knee, is provided with a groove to receive and hold the elasticized adjustable distal sleeve.

As will be understood, the adjustable elasticized distal sleeve will accommodate the contour of the distal residual limb and will readily contract and expand to compensate for changes in volume, particularly in those specific areas which are subject to gross volume changes. In accordance with a further feature of the invention, the sleeve is provided with straps which are threaded through slots in the anterior section and the main support to provide for additional precision adjustment, either tightening or loosening to accommodate the volume fluctuation of the stump. A soft foam pad is included in the sleeve in its distal aspect to provide cushioning contact with the residual limb and to accommodate different stump lengths.

The new and improved fluctuating volume adjustable preparatory below-knee prosthetic socket of the present invention is specially adapted to be mass produced in series for right and left leg shapes and will accommodate virtually all residual limbs in the below-knee category. Since it is readily, easily and reliably adjustable in three dimensions, the new socket design will accommodate all physiological differences in a particular stump size, which is established by the knee diameter when seen in the frontal plane. Thus, the invention allows application of a mass produced prosthetic device without the skills of custom fabrication, therefore, often reducing hospital stays and the concomitant considerable expenses of the rehabilitation process. The new socket is designed for ready mounting of the majority of available prosthetic endoskeletal and foot prosthetic components and may be made ready for application to a patient in minutes.

For a more complete understanding of the present invention and a fuller appreciation of its attendant advantages, reference should be made to the following detailed description taken in conjunction with the accompanying drawings.

DETAILED DESCRIPTION OF THE DRAWINGS

FIG. 4 is cross-sectional view of the new prosthetic socket taken along line 4—4 of FIG. 3;

FIG. 5 is cross-sectional view of the new prosthetic socket taken along line 5—5 of FIG. 3;

FIG. 6 is an exploded perspective view of the new and improved anterior-posterior ratchet adjusting mechanism incorporated in the new prosthetic socket;

FIG. 7 is a cross-sectional view of the anterior-posterior ratchet adjustment mechanism of FIG. 6 taken along line 6—6 of FIG. 2.

DETAILED DESCRIPTION OF THE INVENTION

Figure 1:
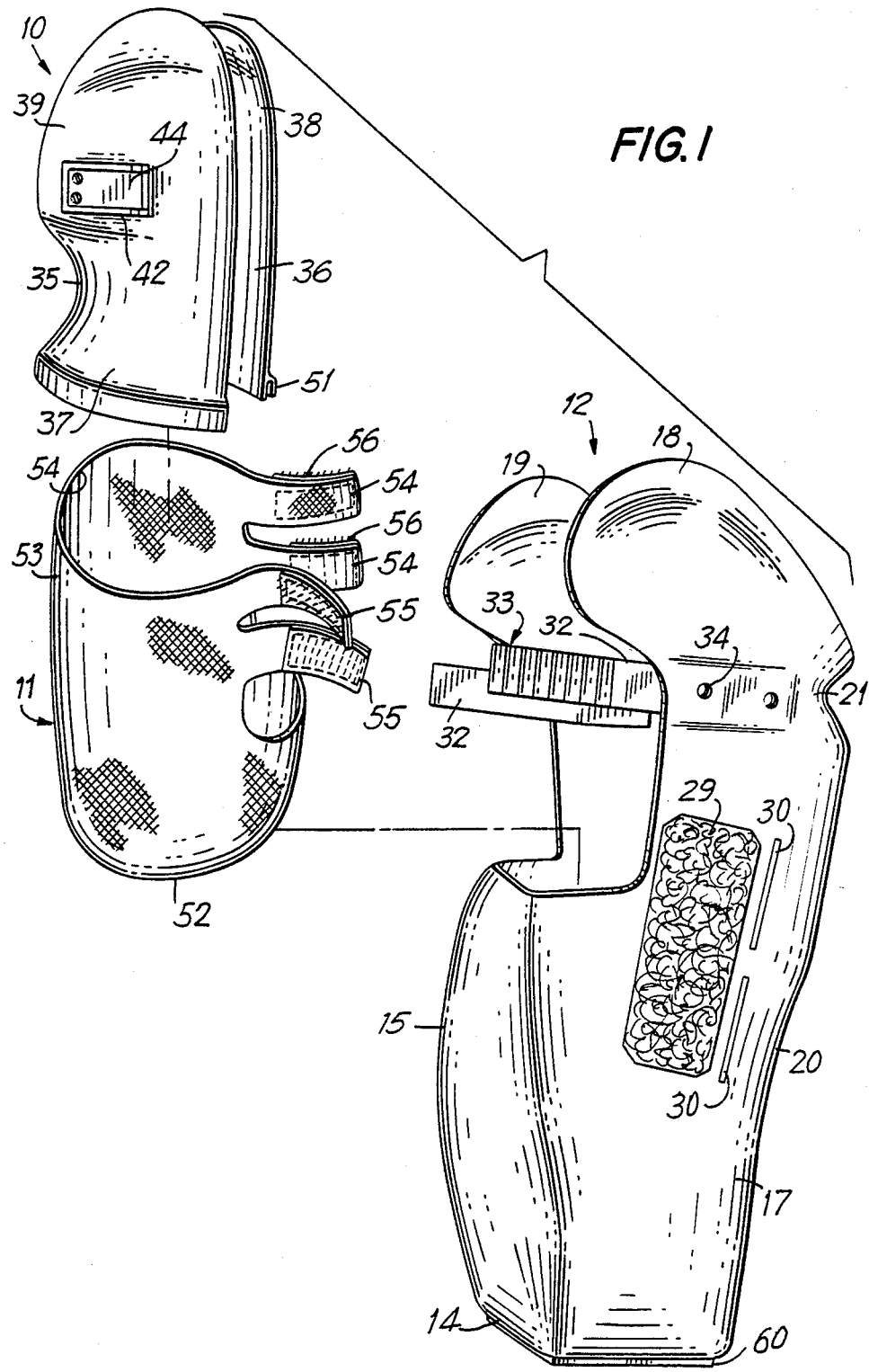
FIG. 1 is an exploded perspective view of the new and improved fluctuating volume adjustable preparatory below-knee prosthetic socket of the present invention.

Referring now to FIG. 1, the new and improved fluctuating volume adjustable preparatory below-knee prosthetic socket of the present invention includes three fundamental components, namely, a posterior popliteal section 10, an elasticized distal sleeve 11, and a main prosthetic support section 12. As will be appreciated, these three elements are combined into a single preparatory below-knee prosthetic socket for mounting a prosthesis, i.e., an artificial limb, to the below-knee stump of an amputee.

The main prosthetic support section 12 is a molded, hollow member of rigid lightweight plastic having a flat bottom wall 14 of generally rectangular configuration. Extending upwardly from the rear edge of the bottom wall is a shaped posterior upper, below knee, calf-engaging wall section 15. The wall 15 has a generally arcuate contour as it extends upwardly towards the knee portion in the vertical plane and it also is of arcuate configuration, as viewed in cross-section, as it extends laterally across the calf. Projecting upwardly from the side edges of the bottom wall 14 are lateral and medial walls 16 and 17, which project upwardly beyond and above the knee joint of the patient. The medial and lateral walls 16 and 17 have oblong condylar support portions 19, 18 extending from anterior portions of the main support section 12 and are contoured to generally conform to the anatomical contours of a leg above the knee. The patella tendon support portion 21 merges with concave knee-engaging portions 18, 19 of the anterior main support wall 20, which, as shown in FIG. 1, projects upwardly from the front edge of the bottom wall 14.

The main support section 12 includes a pair of opposed vertical slots 30 in the lower portions of the medial and lateral walls 16, 17. Secured by adhesive along the rear edges of the walls 16, 17 adjacent the slots 30 are vertical anchoring strips 29 of hooked fastening material ("Velcro"). In accordance with the invention, a pair of stepped ratchet-like adjusting tongues 32 of nylon and having teeth 33 are integrated through recesses 28 to medial and lateral walls 16, 17 in the mid-knee area by screws 34.

Figure 2:
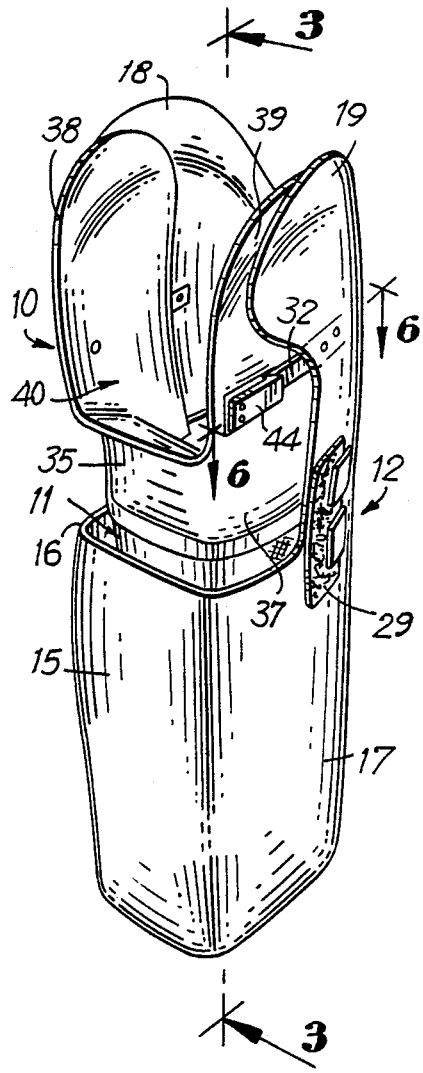
FIG. 2 is a rear perspective view of the new prosthetic socket in its assembled form.
Figure 3:
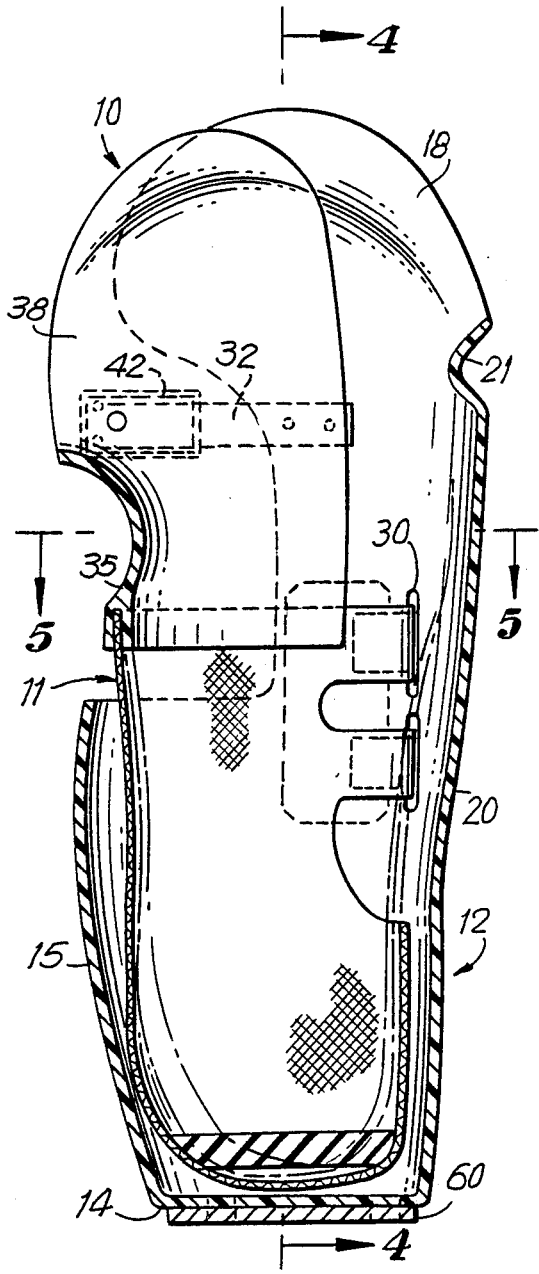
FIG. 3 is cross-sectional view of the new prosthetic socket taken along line 3—3 of FIG. 2.

The posterior popliteal section 10 is fabricated from lightweight rigid plastic, advantageously of the same material employed in the main support section 12, and has an upwardly and outwardly curved posterior wall 35, medial wall 36, and lateral wall 37, joined in a generally C-shaped cross section. The upper portions 38, 39 or supra-condylar extensions of the posterior popliteal walls 35, 36 are contoured similarly to the condylar support portions 18, 19 of the main support section 12. As shown in FIG. 2, the posterior wall of the popliteal support section terminates at mid-knee, leaving an opening 40 at the upper posterior portions of the new socket. Attached by screws 41 to the wall portions 38, 39 are female locking channels 42 adapted to adjustably receive and lock the male adjusting tongues 32 through biased locking spring members 44. The locking spring members 44 as shown in FIG. 7, are fastened in cantilever fashion to the channels by screws 46, and have ratchet-locking teeth 47 formed at the distal ends thereof. The ratchet teeth 47 are biased by the resilience of the members 44 and project through slots 48 in the channels 42 to engage and lock the ratchet teeth 50 integrally formed on the tongues 32.

The lower circumferential edges of the popliteal support 10 are formed to establish a groove 51 for mounting the elasticized sleeve 11, which is formed from elasticized material. The elasticized sleeve 11 is the form of a closed tubular sock having a bottom portion 52, a circular side wall 53. The forwardly facing portions of the wall 53 are cut away and reformed to establish two pairs of opposed fastening strap members 54, 55 which have hooked Velcro fastening tapes 56 sewn on or otherwise adhered to the outer surface portions thereof. The upper edge portions 54 are cemented by a suitable epoxy or otherwise fastened into the corresponding channel 51, as will be understood.

As shown in FIG. 4, a soft foam rubber cushioning pad 56 is disposed freely in the bottom of the elasticized sleeve 11 to contact and to accommodate different length stumps.

In use, and to fit the new prosthetic socket of the present invention to the fluctuating volume stump of a new amputee, the posterior popliteal section 10 with the elasticized sleeve attached and in place, is juxtaposed within the main support section 12, as shown in FIG. 2. More specifically, the ratchet tongues 32 projecting rearwardly from the main section are inserted into the channels 42 where the spring biased locking teeth 33 will engage the locking teeth 47 to lock the posterior section 10 in a desired relationship with the main support 12. In accordance with the invention, the relationship of the posterior section 10 and anterior main section 12 may be precisely adjusted in small (5 mm) increments representing the width of each of the locking teeth 33 on the male locking members 32. FIGS. 6 and 7 show, with greater specificity, the manner in which the locking teeth 47 are flexed for adjustment as they engage and lock with the locking teeth 33.

Figure 8:
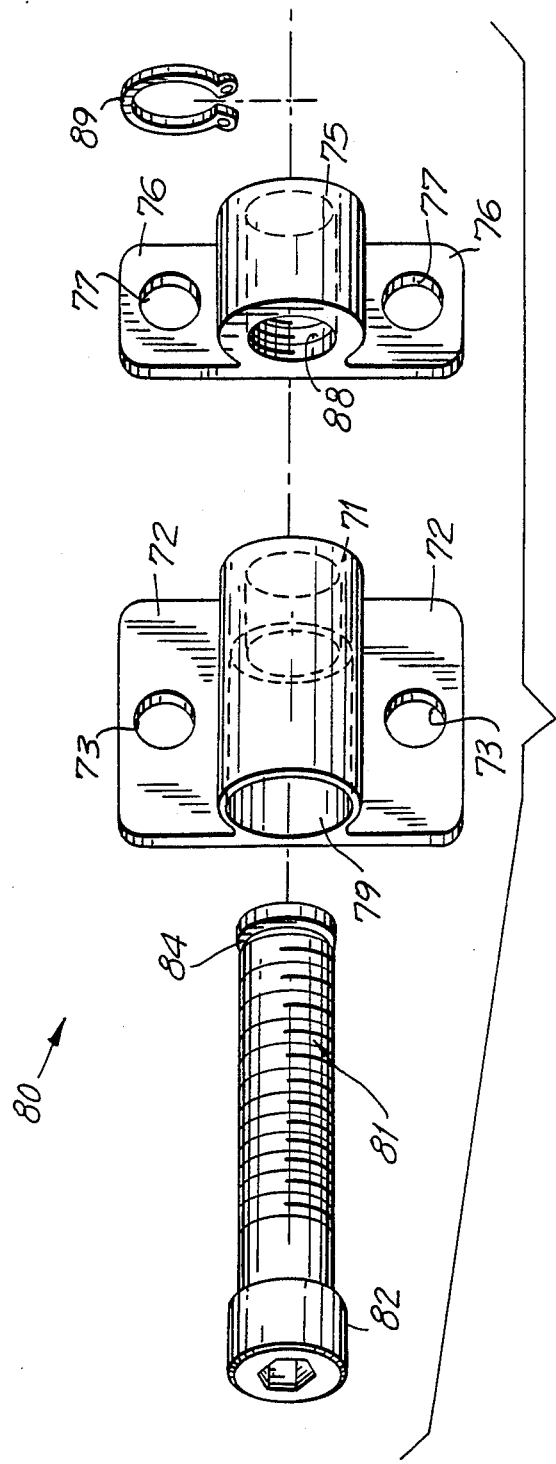
FIG. 8 is an exploded view of an anterior-posterior screw jack adjustment mechanism which may be substituted for the ratchet mechanism.

In lieu of the employment of the anterior-posterior ratchet locking mechanism shown in FIGS. 6 and 7, the relationship of the posterior section 10 with the anterior main section 12 may be infinitely adjusted by use of a pair of anterior-posterior (A-P) screw jack mechanisms 70 illustrated in FIG. 8. The A-P adjustment mechanism 70 includes an anterior cylindrical housing 71 having flanges 72, which are fastened to the exterior surfaces of the main section 12 through screw holes 73 in the region where the ratchet tongues were mounted in the above-described embodiment of FIG. 1. A posterior cylindrical housing 75, having flanges 76, is fastened to the posterior popliteal section 10 through screw holes 77 in the region where channels 42 were mounted in the embodiment of FIG. 1.

As shown, a screw jack 80, having external threads 81, an enlarged head 82 with a hexagonal driving socket 83 formed therein, and an annular locking groove 84 is adapted to cooperate with housings 71, 75 as follows. The screw jack 80 is inserted through the housing 71 where the head 82 will be disposed for selective rotation in opening 79 with the underside 85 of the head bearing against shoulder 78 formed in the housing 72. The exterior threads 81 are threaded into a mating threaded opening 88 formed interiorly of housing 75. With the screw jack 80 threaded through the housing 75 a C-clip 89 is slipped into the channel 84 to limit travel of the jack 80 with respect to the housing 75.

As will be understood, rotation of the screw jack 80 by a hexagonal allen wrench in the socket 83 will displace the housing 75 with respect to the housing 71, causing precise anterior-posterior adjustment of the sections 10, 12 to which the housings are secured.

As shown in FIGS. 4 and 5, the flaps 54, 55 of the elasticized sleeve 11 are threaded through the slots 30 of main support member 12 and are then rearwardly folded, in a fulcrum-like manner with respect to the rear edges of the slots 30, where the hooked Velcro tapes 56 may be fastened to the looped Velcro anchoring strips 29 in a precisely adjusted manner in accordance with the principles of the invention.

At the very bottom of the main section 12, a metal interfacing plate 60 is fastened by appropriate fastening means such as screws (not shown). The plate 60 has threaded holes for receiving prosthetic components in the form of an artificial limb of the proper length for the particular patient to whom the new socket has been fitted.

It will be appreciated that the new and improved prosthetic temporary socket of the present invention may be manufactured in a series of three or four sizes and may be employed "off the shelf" to fit a new amputee, without the necessity of custom manufacture of a precisely multi-dimensional socket for mounting prosthetic components. Because the new and improved ratchet mechanism and screw jack mechanism accommodate very finite and precise adjustment of the posterior popliteal section with relation to the anterior support section, precise and sensitive adjustment may be made in that region for securing of the prosthetic socket for securing the same to the stump of a patient, notwithstanding the rather dynamic changes in the volume of the stump that occur during the post-operative healing process. Similarly, and importantly, further adjustments in the nature of precise and comfortable fitting of the socket to the healing and fluctuating stump is provided through the engagement of the elasticized sleeve with the stump and the tightening or loosening of the same by adjusting the degree of tension on the stump through the tightening and loosening of the straps 54, 55 as they are pulled and/or retracted through the slots 30 before being folded backwardly and secured to the anchoring Velcro strip 29.

It should be understood, of course, that the specific form and arrangement of the present invention herein illustrated and described is intended to be representative only, as certain changes may be made therein, without departing from the clear teachings of the disclosure. Accordingly, reference should be made to the following claims in determining the full scope of the invention.

We claim:

1. A fluctuating volume adjustable prosthetic socket for below-the-knee amputees, comprising
   (a) a generally hollow main body support of rigid plastic;
   (b) said main support having a generally flat rectangular bottom wall, an anterior wall, a posterior wall, and medial and lateral walls forming a cavity to receive a residual limb;
   (c) a posterior popliteal section of rigid plastic generally contoured to conform to the posterior anatomy of the knee;
   (d) said popliteal section including a lower curved posterior wall merging in generally U-shaped cross section with medial and lateral popliteal walls each having supracondylar extension;
   (e) the uppermost portions of said main support medial and lateral walls including supracondylar support portions;
   (f) said posterior section nesting within said main support section with patella tendon support portions generally juxtaposed with said supracondylar extensions;
   (g) cooperating locking means disposed on said posterior section and said main support section for adjustably joining said sections for controlled limited anterior-posterior displacement with respect to each other in which
      (i) said locking means is a screw jack mechanism including an anterior housing, a posterior housing, and an elongated cylindrical threaded screw;
      (ii) one of said housings having a threaded portion adapted to mate with said screw;
      (iii) the other of said housings mounting the free end of said screw;
      (iv) whereby rotation of said screw in one of said housings will effect the relative displacement of said two housings by the advancement or retraction of said threaded screw in said threaded portion;
   (h) elasticized sleeve means supported at lower portions of said posterior popliteal section;
   (i) adjusting means associated with said sleeve means for controlling the diameter and snugness of said sleeve means on a residual limb;
   (j) whereby the volume of the residual limb receiving cavity defined by the combination of the main support section, posterior popliteal section, and sleeve means may be readily and precisely adjusted to compensate for changes in volume of a residual limb to be received therein.

2. The prosthetic socket of claim 1, in which
   (a) said adjusting means for said sleeve means includes sleeve straps projecting forwardly therefrom;
   (b) slots are formed on said anterior wall of said man support section;
   (c) first anchoring fastening tape means are mounted adjacent said anterior edges of said slots;
   (d) second cooperating fastening tape means are fixed to the free ends of said sleeve straps;
   (e) whereby said straps may be threaded through said slots, folded rearwardly back toward said anchoring fastening tape means and selectively secured thereto for adjusting the diameter and snugness of said sleeve means.

3. The prosthetic socket of claim 2, in which
   (a) a foam pad stump engaging support is disposed within said sleeve means.

4. The prosthetic socket of claim 3, in which
   (a) a prosthetic mounting plate means is secured to said bottom wall of said main support section;
   (b) said plate means being adapted to mount a prosthetic limb to said main support section.

5. A fluctuating volume adjustable prosthetic socket for below-the-knee amputees, comprising.
   (a) a generally hollow main body support of rigid plastic;

(b) said main support having a generally flat rectangular bottom wall, an anterior wall, a posterior wall, and medial and lateral walls forming a cavity to receive a residual limb;
(c) a posterior popliteal section of rigid plastic generally contoured to conform to the posterior anatomy of the knee;
(d) said popliteal section including a lower curved posterior wall merging in generally U-shaped cross section with medial and lateral popileal walls each having supracondylar extensions;
(e) the uppermost portions of said man support medial and lateral walls including supracondylar support portions;
(f) said posterior section nesting within said main support section with patella tendon support portions generally juxtaposed with said supracondylar extensions;
(g) cooperating locking means disposed on said posterior section and said main support section for adjustably joining said sections for controlled limited anterior-posterior displacement with respect to each other, in which
  (i) said locking means is a ratchet means including a pair of nylon tongue means affixed to said main section and projecting rearwardly thereof and a mating pair of channel means affixed to said posterior section;
  (ii) said tongue means including a series of ratchet teeth;
  (iii) said channel means including a biased locking spring member having a locking tooth;
  (iv) said locking spring member is mounted in cantilever fashion exteriorly of said channel means with said locking tooth projecting through an opening therein to engage and to lock selectively with teeth of said tongue means when said tongue means is inserted into said channel;
(h) elasticized sleeve means supported at lower portions of said posterior popileal section;
(i) adjusting means associated with said sleeve means for controlling the diameter and snugness of said sleeve means on a residual limb;
(j) whereby the volume of the residual limb receiving cavity defined by the combination of the main support section, posterior popliteal section, and sleeve means may be readily and precisely adjusted to compensate for changes in volume of a residual limb to be received therein.

6. The prosthetic socket of claim 5, in which
(a) said adjusting means for said sleeve means includes sleeve straps projecting forwardly therefrom;
(b) slots are formed on said anterior wall of said main support section;
(c) first anchoring fastening tape means are mounted adjacent said anterior edges of said slots;
(d) second cooperating fastening tape means are fixed to the free ends of said sleeve straps;
(e) whereby said straps may be threaded through said slots, folded rearwardly back toward said anchoring fastening tape means and selectively secured thereto for adjusting the diameter and snugness of said sleeve means.

7. The prosthetic socket of claim 6, in which a foam pad stump engaging support is disposed within said sleeve means.

8. The prosthetic socket of claim 7, in which
(a) a prosthetic mounting plate means is secured to said bottom wall of said main support section;
(b) said plate means being adapted to mount a prosthetic limb to said main support section.

* * * * *